(12) United States Patent
Legerton et al.

(10) Patent No.: US 7,918,558 B1
(45) Date of Patent: Apr. 5, 2011

(54) SYSTEM AND METHOD FOR TESTING RETINAL FUNCTION

(75) Inventors: Jerome A. Legerton, San Diego, CA (US); Akos Feher, Playa del Rey, CA (US); Janos Feher, Budapest (HU)

(73) Assignee: Preventive Ophthalmics, Playa del Ray, CA (US)

( * ) Notice: Subject to any disclaimer, the term of this patent is extended or adjusted under 35 U.S.C. 154(b) by 0 days.

(21) Appl. No.: 12/841,849

(22) Filed: Jul. 22, 2010

(51) Int. Cl.
*A61B 3/10* (2006.01)

(52) U.S. Cl. .................................. 351/211; 351/246

(58) Field of Classification Search .................. 351/211, 351/246, 209, 210, 212, 205, 221
See application file for complete search history.

(56) References Cited

U.S. PATENT DOCUMENTS

| | | | |
|---|---|---|---|
| 4,493,539 A * | 1/1985 | Cannon, Jr. ................ | 351/205 |
| 4,861,154 A * | 8/1989 | Sherwin et al. ............ | 351/205 |
| 4,953,968 A * | 9/1990 | Sherwin et al. ............ | 351/211 |

FOREIGN PATENT DOCUMENTS

WO   WO 2004/112597   12/2004

* cited by examiner

*Primary Examiner* — Hung X Dang
(74) *Attorney, Agent, or Firm* — Sheppard Mullin Richter & Hampton LLP; David E. Heisey

(57) ABSTRACT

A method of measuring retinal or visual pathway function comprises stimulating optokinetic nystagmus by presenting a visual stimulus to a patient; modifying a first parameter of the visual stimulus; modifying a second parameter of the visual stimulus; and using the modified visual stimulus to determine a threshold stimulus for optokinetic nystagmus; wherein the first and second parameters are selected from a group of parameters comprising a pattern for the visual stimulus, a width of the visual stimulus, a distance between the visual stimulus and the patient, a spatial frequency of the visual stimulus, a rate of change or temporal frequency of the test face of the visual stimulus, and a contrast between elements of the visual stimulus.

41 Claims, 11 Drawing Sheets

SYSTEM AND METHOD FOR TESTING RETINAL FUNCTION

TECHNICAL FIELD

The present invention relates generally to eye care, and more particularly, some embodiments relate to retinal testing using evoked optokinetic nystagmus.

DESCRIPTION OF THE RELATED ART

Traditional retinal function tests have difficulty testing for early detection of age related macular degeneration, for diagnosing malingering, and for vision testing in non-communicative patients, such as infants, toddlers, patients with neurological deficits or cognitive disorders, and animals.

Optokinetic nystagmus (OKN) is the eye movement elicited by the tracking of a moving field. It is characterized by an alternating smooth pursuit in one direction and saccadic movement in the other direction. Pervious attempts have failed to demonstrate a relationship between OKN and visual acuity.

BRIEF SUMMARY OF EMBODIMENTS OF THE INVENTION

According to various embodiments of the invention, a system and method for testing retinal function or visual acuity utilizes variations in OKN response to changing visual stimuli. Testing includes presenting a test face to a patient comprising a plurality of contrasting parallel bars. A number of different variables may be modified during testing, such as width of the test face, distance from the test face to the eye, spatial frequency of the test face, rate of change or temporal frequency of the test face, contrast of the test face, and wavelength (color) of the test face.

According to an embodiment of the invention a method of measuring retinal or visual pathway function comprises stimulating optokinetic nystagmus by presenting a visual stimulus to a patient; modifying a first parameter of the visual stimulus; modifying a second parameter of the visual stimulus; and using the modified visual stimulus to determine a threshold stimulus for optokinetic nystagmus; wherein the first and second parameters are selected from a group of parameters comprising a pattern for the visual stimulus, a width of the visual stimulus, a distance between the visual stimulus and the patient, a spatial frequency of the visual stimulus, a rate of change or temporal frequency of the visual stimulus, and a contrast between elements of the visual stimulus.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF. DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

The present invention is directed toward a system and method for providing a visual system diagnostic test. A test target visual stimulus is presented to a patient to induce the optokinetic nystagmus (OKN) response in the patient. Various parameters of the test target are modified in a predetermined manner to determine a threshold stimulus for OKN in the patient in terms of values of the parameters. The threshold stimulus values provide diagnostic information for visual acuity or visual or retinal system functioning for patients, such as non-verbal humans, or animals that would otherwise be unable to be diagnosed.

In further embodiments, an intervening stimulus, such as a photostress or pharmaceutical, is provided to disrupt the OKN response in the patient. Further diagnostic information may be obtained from the OKN recovery time and OKN threshold parameter values after OKN recovery.

Figure 1:
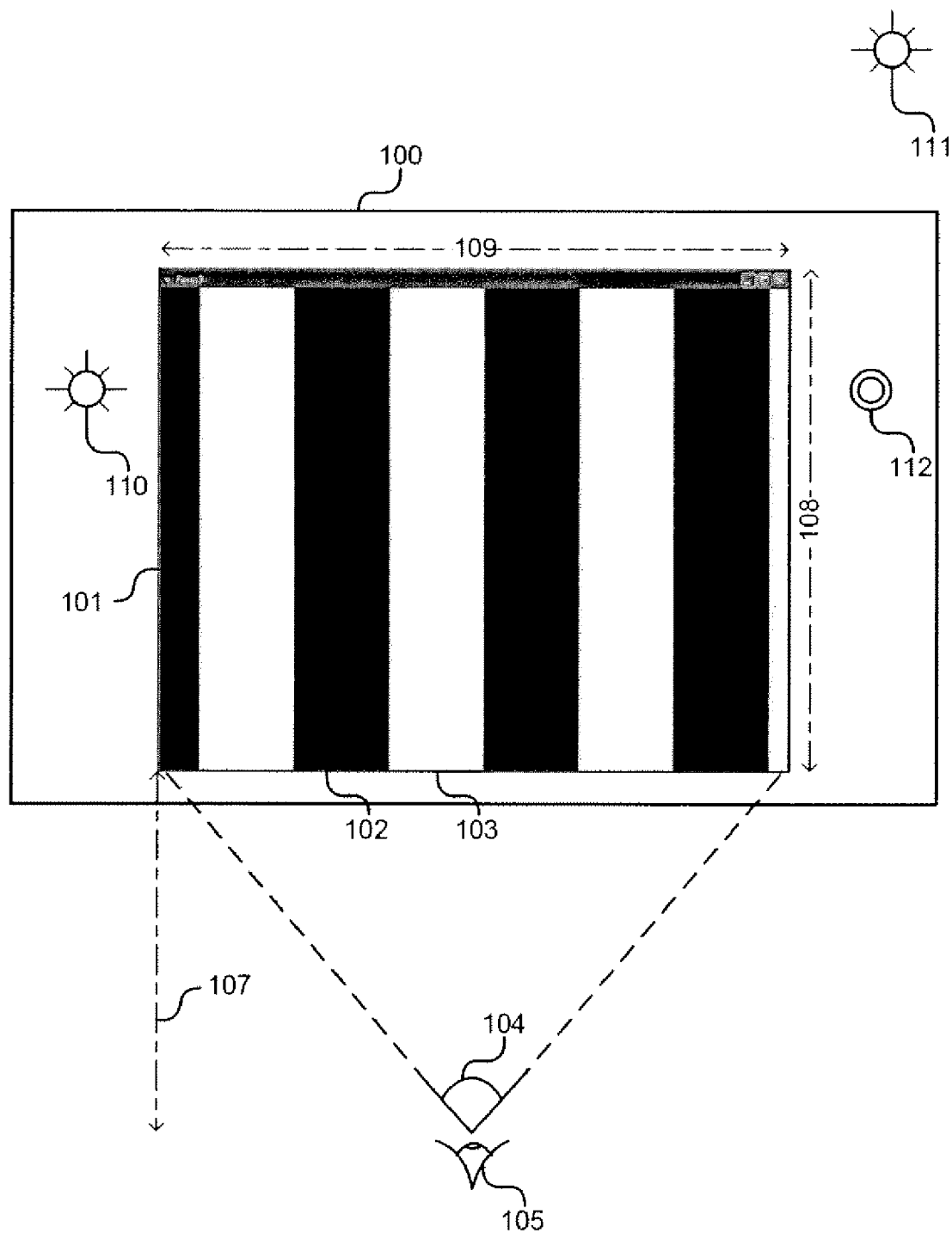
FIG. 1 illustrates a OKN testing setup implemented in accordance with an embodiment of the invention.

FIG. 1 illustrates an OKN testing setup implemented in accordance with an embodiment of the invention. A visual stimulus 101 is presented to a patient 105. The visual stimulus 101 comprises a test target including a dynamic pattern that is designed to elicit an OKN response in the patient. The test target is displayed on a display screen 100, which might be a projection screen, television display, computer display, wearable display, head mounted display, hand held display or other display. Such wearable displays, may incorporate optics in the conventional manner to provide refractive correction for the focal demand of the display distance from the eye. Further, the wearable display may incorporate a contact lens for correction of the focal demand. In some embodiments, the display 100 may be configured to encompass the entire field of vision, for example in the case of a head mounted display or display integrated into contact lenses. In other embodiments, the display 100 may fill only a portion of the patient's field of view.

In the illustrated embodiment, the visual stimulus 101 comprises a plurality of parallel bars 102, 103 that are colored or saturated in an alternating, contrasting manner. The test pattern has a rate of change or temporal frequency of the test face that causes the parallel bars 102, 103 to move to the left or to the right within the test target 101. This apparent motion induces the OKN response in the patient 105. The distance 107 from the patient 105 and the width 109 of the visual stimulus 101 determine the horizontal angle 104 subtended by the stimulus 101 at the eye 105. Similarly, the height 108 of the stimulus 101 and the distance 107 from the stimulus 101 to the eye 105 determine the vertical angle subtended by the stimulus 101 at the eye 105.

Figure 2:
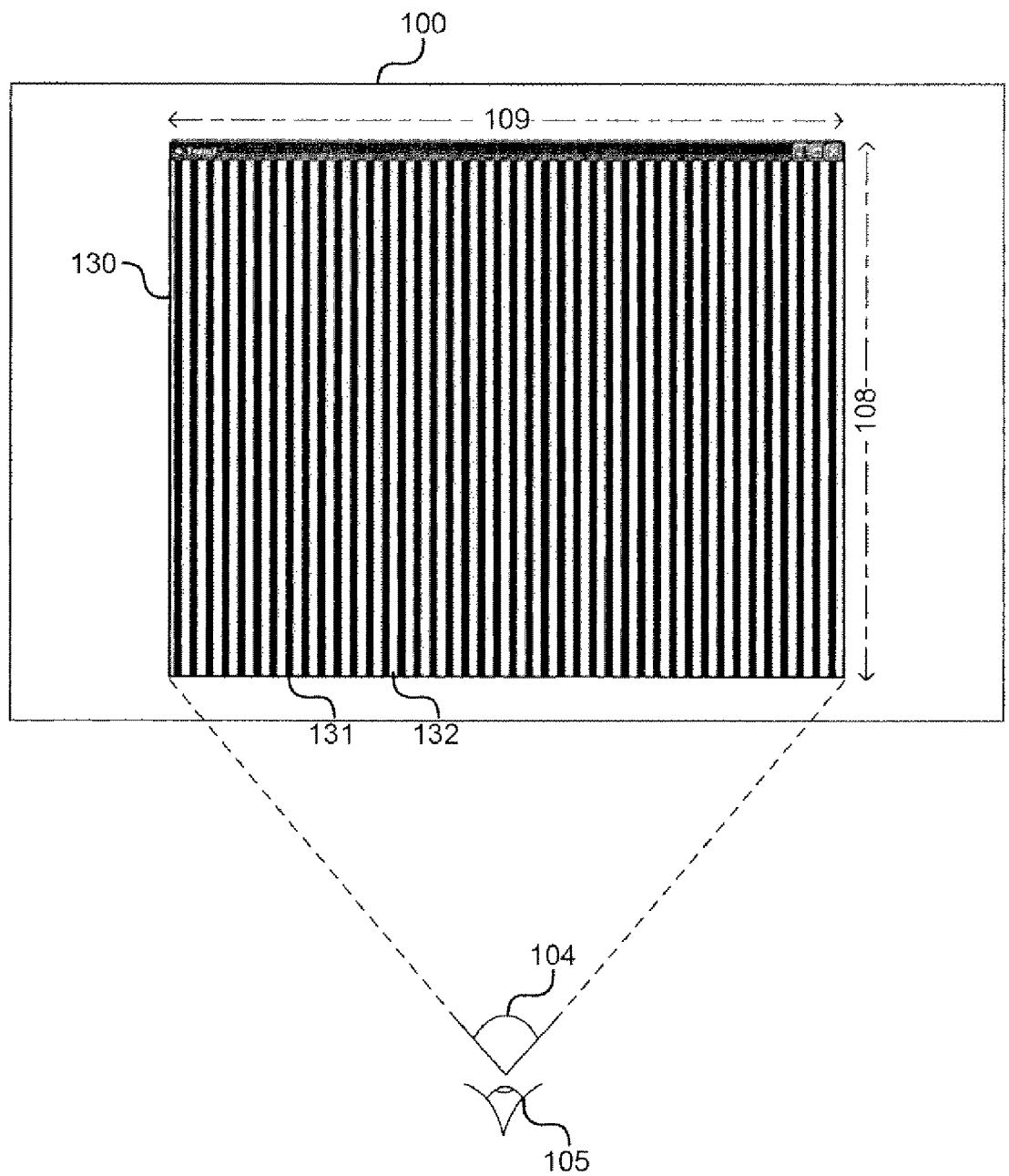
FIG. 2 illustrates an OKN testing setup demonstrating a visual stimulus with an increased spatial frequency.

The widths of the bars 102, 103 or area 109×108 of the stimulus 101 determine a spatial frequency for the visual stimulus. The stimulus 130 illustrated in FIG. 2 has a higher spatial frequency than the visual stimulus 101 in FIG. 1. As illustrated, at the same area 109×108, the smaller widths of the parallel bars 131, 132 results in a higher spatial frequency for the stimulus 130 than the stimulus 101. The combined width of one light bar and one dark bar constitutes one cycle. The spatial frequency is computed as the number or fraction of one cycle per degree of angle subtended at the eye.

Figure 3:
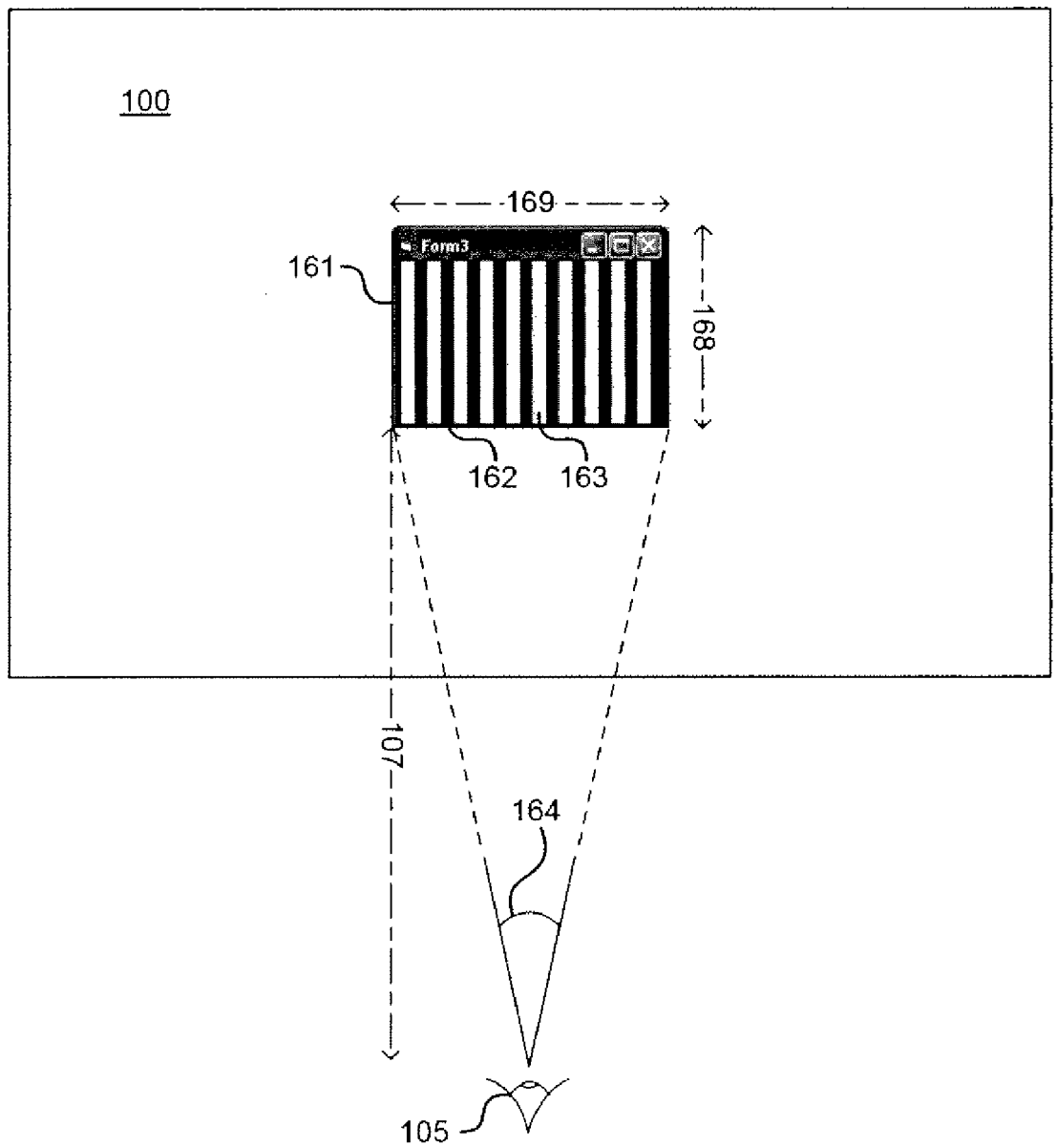
FIG. 3 illustrates an OKN testing setup demonstrating a visual stimulus with a reduced area.
Figure 4:
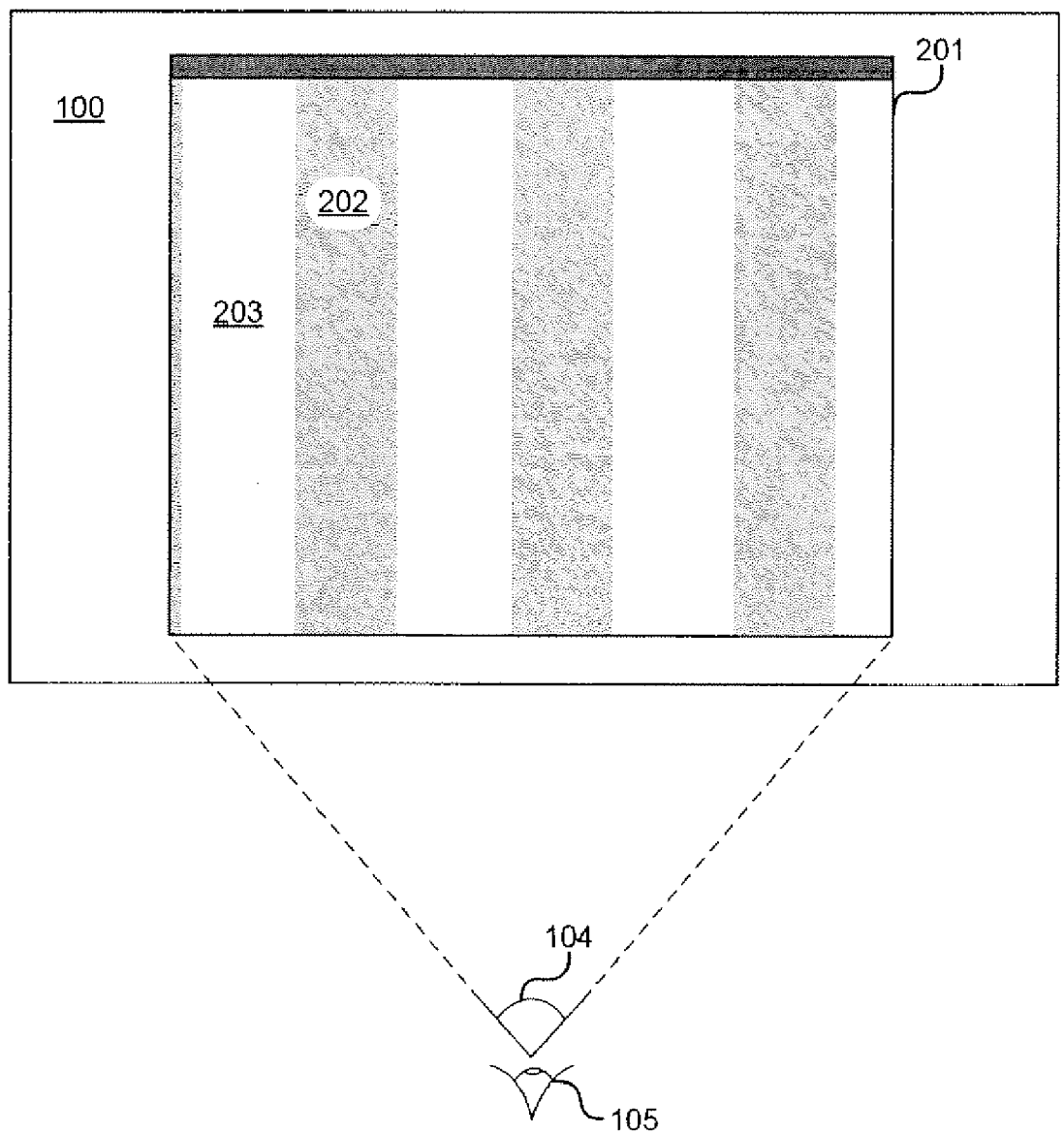
FIG. 4 illustrates a stimulus having a reduced contrast ratio.

In some embodiments, other parameters of the visual stimulus can be modified. For example, FIG. 3 illustrates a stimulus 161 having a reduced width 169 and height 168 compared to the width and height of the stimulus 101. Accordingly, at the same test distance 107, the angle 164 subtended by the stimulus test face 101 with respect to the patient 105 is reduced. FIG. 4 illustrates a stimulus having a reduced contrast ratio between adjacent bars 202 and 203. In further embodiments, the patterns may employ elements having range of contrasts and elements having different colors or shades. In some embodiments, a contrast threshold OKN can be measured for each eye. Such a contrast threshold can be reported in a contras, a temporal frequency, an angle of subtended test face and a spatial frequency. A contrast threshold OKN is useful as a baseline measure for an individual before photostress or other intervention is presented to measure a change in visual function with the respective intervention.

Figure 5:
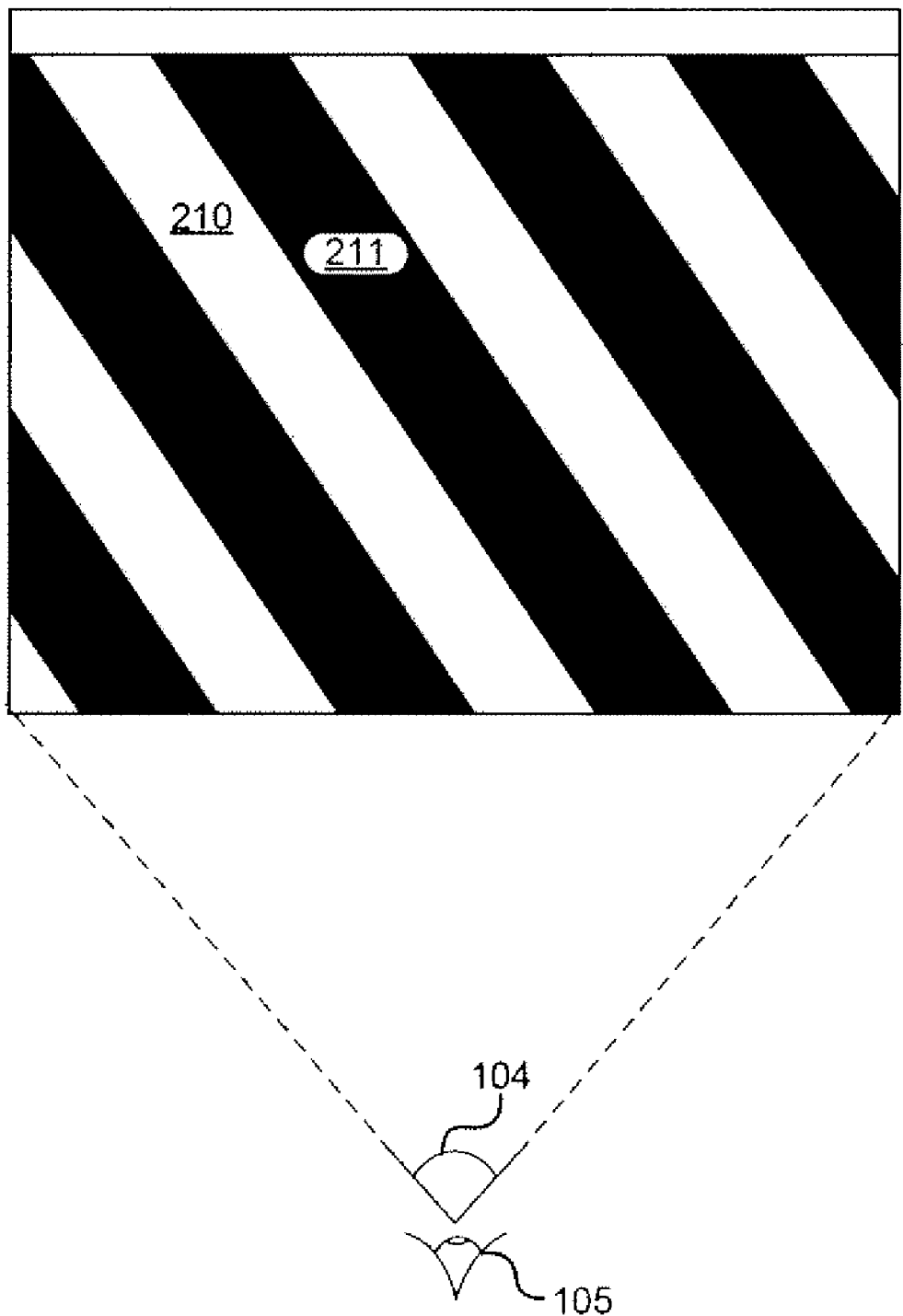
FIG. 5 illustrates a stimulus having an oblique bar pattern.
Figure 6:
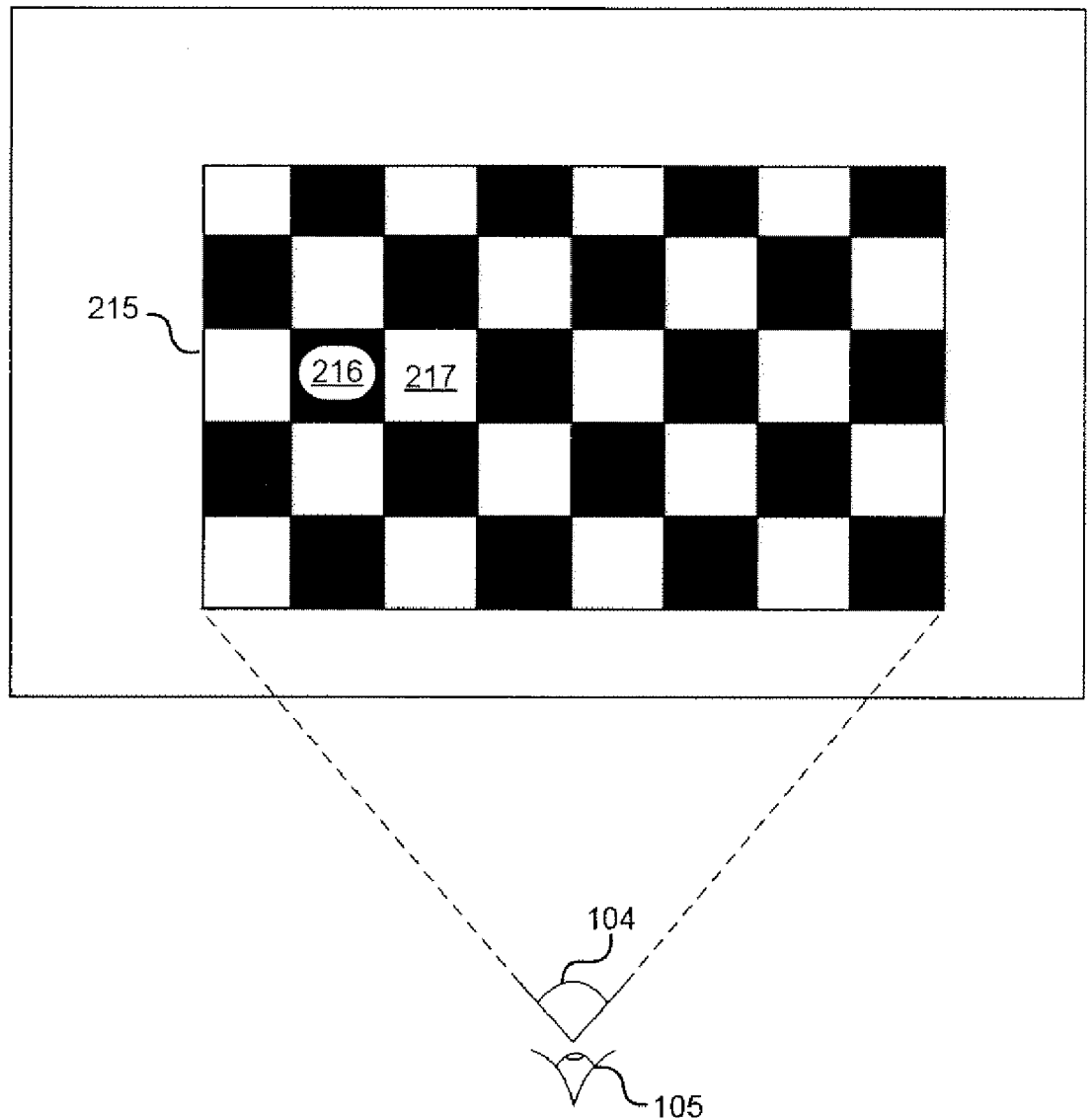
FIG. 6 illustrates a stimulus having a rectilinear grid pattern.
Figure 7:
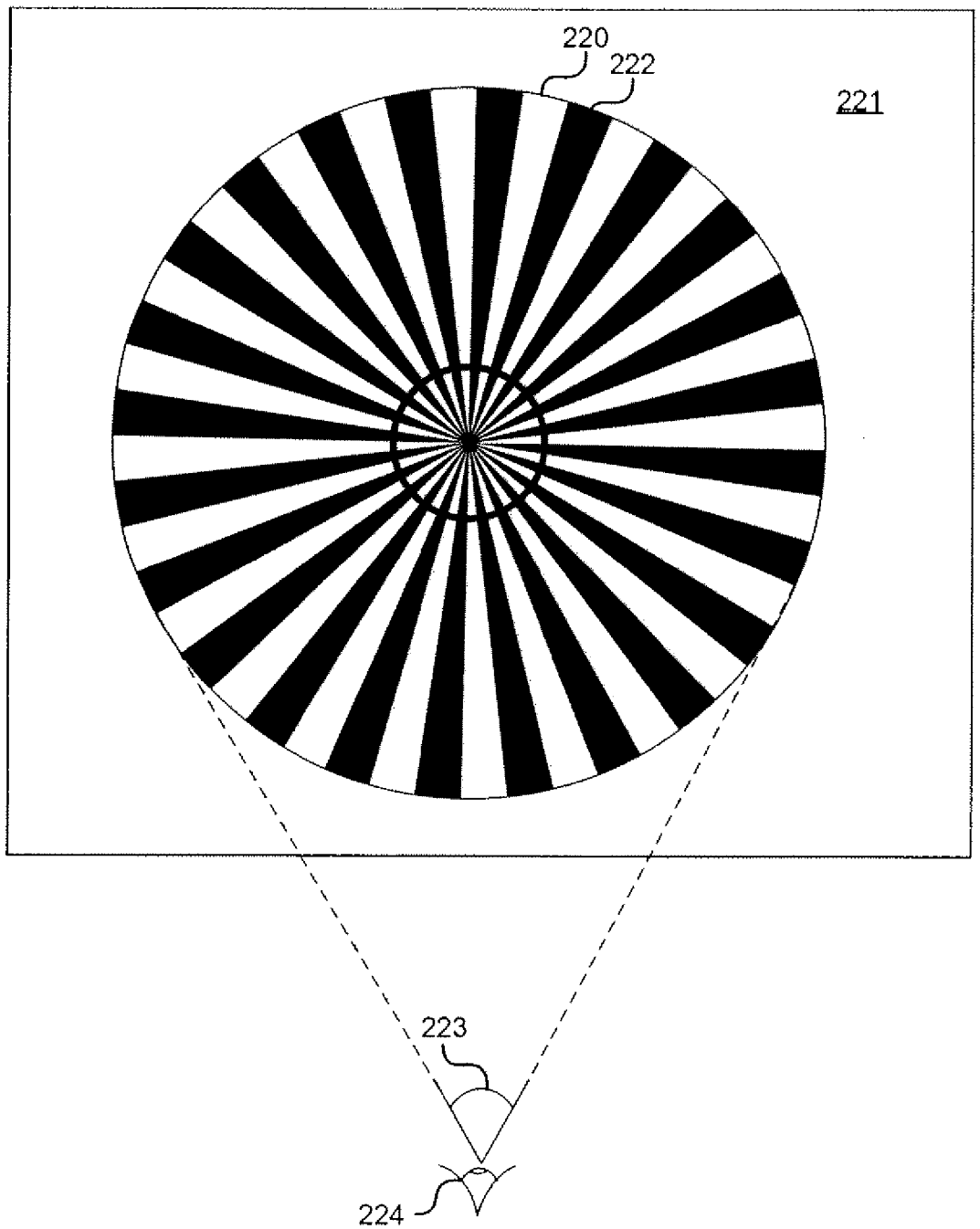
FIG. 7 illustrates a stimulus having a curvilinear pattern.

Various embodiments may also employ different test patterns. For example, instead of parallel vertical bars, a test pattern may employ parallel horizontal bars, or oblique parallel bars such as bars 210, 211 of FIG. 5. Other test patterns might include a rectilinear grid test pattern such as checkerboard 215 made up of alternating contrasting boxes 216, 217, illustrated in FIG. 6, or a curvilinear test pattern, such as pattern 220 illustrated in FIG. 7.

Figure 8:
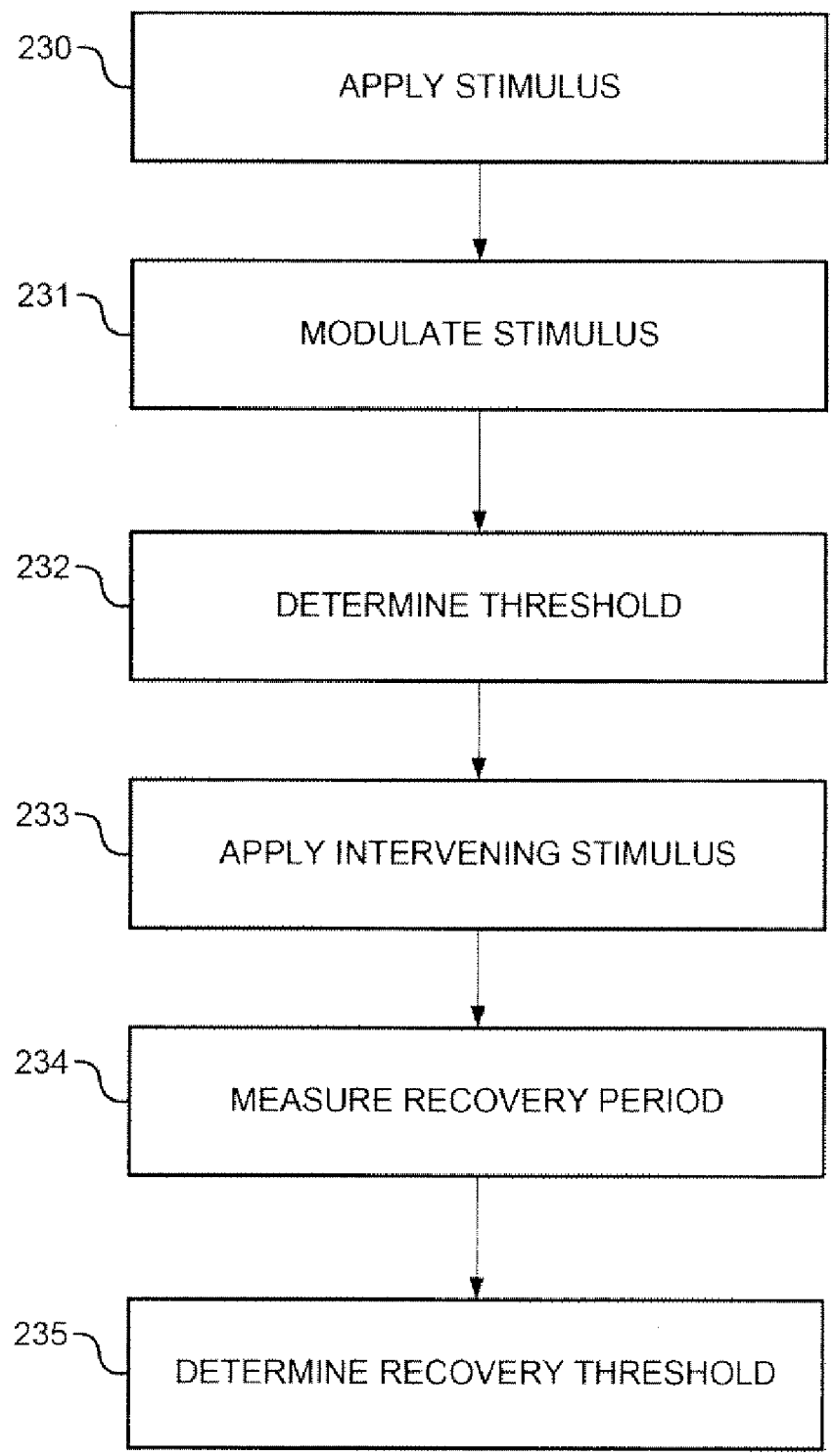
FIG. 8 illustrates a testing method according to an embodiment of the invention.

FIG. 8 described a method of OKN visual testing implemented in accordance with an embodiment of the invention. In step 230, a visual stimulus, such as a test target, is presented to a patient to elicit an OKN response. In step 231, parameters of the visual stimulus are modified to determine a threshold OKN response stimulus for the patient in step 232. For example, a modulation step 231 might comprise increasing the spatial frequency of parallel bar test target (thereby decreasing the width of the bars) to determine the threshold spatial frequency for the OKN response. During this modulation step 231, when a first parameter is changed, a second parameter is simultaneously modified.

In a particular embodiment, spatial frequency of the target is increased, then the rate of change or temporal frequency of the test face of the target is also slowed. In other words, as the bars become more narrow and the spacing decreases, the speed of the test target path is decreased. The temporal frequency in this case is the number of cycles or fraction of a cycle which pass a datum or reference point on the display screen per second. A correlation between conventional minimum angle of resolution (MAR) visual acuity measures and OKN response thresholds has been determined when the speed of the pattern is decreased as the spatial frequency is increased. Accordingly, an OKN threshold value comprising a speed value in cycles per second and spatial resolution value n cycles per degree may be found to correlate with a patient's visual acuity when measured as a minimum angle of resolution using conventional optotypes. For example, in one test, a threshold value for OKN response occurred using a target with a face width of 21.8° at the viewer's eye when the spatial frequency is 0.26°/cycle and the temporal frequency is 2.23°/second, where one cycle is from the beginning to the end of a contrasting pair of bars.

In another embodiment, the rate of change or temporal frequency of the test face and the width of the test face or angle subtended are modified simultaneously. Previously, investigators have reported that the test distance must approach optical infinity to provide some value in predicting visual acuity with evoked OKN and that the angle subtended by the test face must be sufficiently large. Conversely, we discovered that there appeared to be less importance with regard to the test distance or the angle subtended by the test face at the eye than there is to the speed of the test target as a function of the angle subtended by the test face at the eye. Further, small test face angles and reduced test distances may be employed when the temporal frequency is decreased as a function of the angle subtended by the test face at the eye. It was discovered that very small test faces can be used when the speed is modulated as a function of the test face width. As a result, a smaller test face may be used to increase the spatial frequency when the test speed is reduced. For example, the test described above, a decrease in test face width from 21.8° to 5.62° resulted in a threshold OKN response at a spatial frequency of 0.156°/cycle and at a temporal frequency of 1.149°/second.

In a further embodiment, the test distance and the spatial frequency are modified simultaneously. A relationship was discovered with regard to the test distance and the spatial frequency of the test target. Consistent with conventional MAR measures, the threshold OKN spatial frequency decreased as the test distance increased.

In still further embodiments, contrast and spatial frequency; contrast and temporal frequency; stimulus color and contrast; spatial frequency and color; or any other combination of parameters may be modified simultaneously.

In some embodiments, the step of modulating the stimulus 231 might comprise modifying the combination of parameters in a predetermined manner. For example, a predetermined battery of modified stimuli may be presented, or various parameters of the stimulus may be modified in a continuous fashion. Additionally, or alternatively, a system user, such as a practitioner, may use system controls to modify the parameters in a desired fashion.

In further embodiments, once an initial threshold for OKN is determined, an intervening stimulus 233 is presented to the patient to disrupt the OKN response. Such intervening stimuli may comprise photostress stimuli, chemical or pharmaceutical stimuli, ambient room illumination, focal demand independent of test distance, or auditory, kinesthetic or visual tasks or challenges. In some embodiments, multiple intervening stimuli may be applied to a patient during testing. For example, a photostress stimulus may be presented to completely disrupt the OKN response, while a auditory task is presented during the recovery period to determine effects on recovery. In some embodiments, the photostress may be a created in an uninterrupted form of a predetermined area, intensity and duration or in the form of a strobe or flickering stimulus. For example, a photostress stimulus may be presented by causing the test face with the vertical bar or other pattern to flicker or by way of a strobing effect of the unsaturated bars or elements of the test face stimulus. The flicker or strobe effect may be set at a predetermined frequency or modulated until the photostress interrupts the OKN response.

FIG. 1 illustrates two possible photostress illumination devices 110 and 111. In some embodiments, a photostress 110 may be applied in the same plane as the display 100, while in other embodiments, a photostress 111 may be applied off plane with the display 100.

After the patient's OKN response has been interrupted in step 233, the patient is monitored for recovery of OKN. In step 234, the time it takes for OKN recovery is measured. Such testing may be useful in the early detection or monitoring of patients and their treatment with multiple sclerosis, Alzheimer glaucoma, Parkinson's or other diseases associated with apoptosis or those known to affect the vestibular apparatus. In further embodiments, the threshold stimulus for OKN may vary after recovery, or after some predetermined amount of recovery. In these embodiments, the threshold stimulus for OKN response after recovery is measured (step 235). In some embodiments, the recovery may comprise some predetermined amount of time, or some amount of OKN recovery less than complete recovery. For example, a practitioner may measure the threshold OKN stimulus after 80% of normal recovery time to determine the patient's rate of recovery. As another example, a practitioner may apply photostress and then measure time until recovery of minimal OKN response, and then further measure time until complete OKN recovery.

Figure 9:
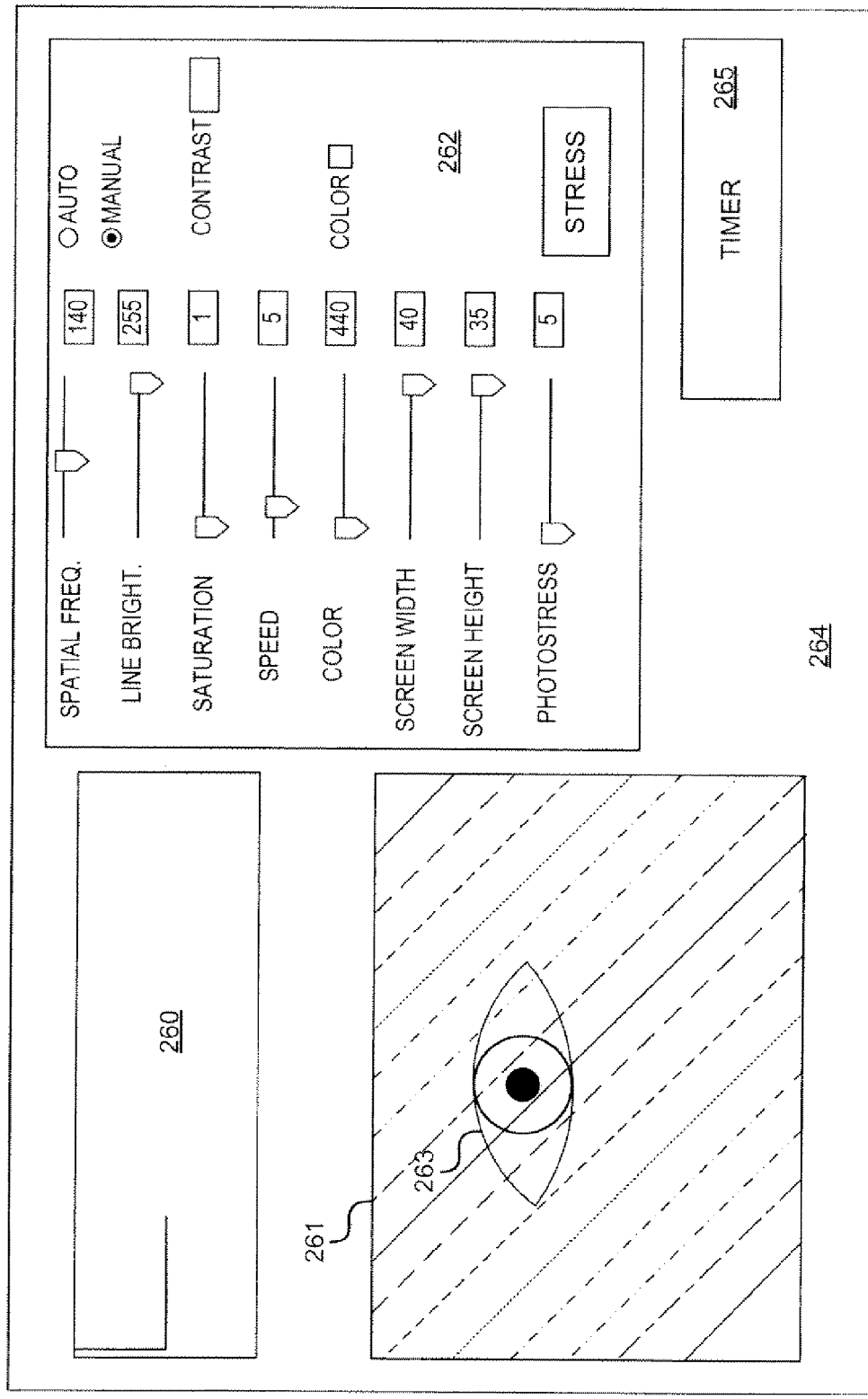
FIG. 9 illustrates a testing user interface implemented in accordance with an embodiment of the invention.

FIG. 9 illustrates an example user interface (UI) for OKN testing implemented in accordance with an embodiment of the invention. In this embodiment, UI 264 is presented on a display to a system user, where the display is coupled to a computer system that controls the OKN testing system presented to the patient. A display field 261 shows the user an image of the patient's eye 263. For example, in FIG. 1, a camera 112 is disposed in the testing system to record the movements in the eye 105, which is then displayed as image 263. In some embodiments, the computer system may be configured to automatically track the eye's movement during testing to determine when OKN is occurring. In other embodiments, the visual field 261 may be used by the system user to determine if OKN occurs.

Field 260 illustrates a simplified display of the patient's eye movements. A first curve tracks the patient's eye movements, where a sinusoidal movement confirms OKN response. A second curve indicates the spatial frequency of the stimulus image as a sinusoidal curve. Superposing these two curves gives an additional visual confirmation that the test image is causing OKN.

A system parameter field 262 allows the user to modify various parameters of the OKN test system. As discussed above, various parameters may be modified during testing, such as spatial frequency, test figure brightness, saturation, contrast speed, color, test figure width, test figure height, photostress time duration, or photostress brightness. In some embodiments, the system may be configured to automatically vary some parameters as other parameters are changed. For example, speed or temporal frequency may be automatically modified as the user modifies spatial frequency. In further embodiments, the parameters may be manually modifiable. For example, the system may automatically modify the speed as the user modifies the spatial frequency until the patient nears the threshold stimulus. Then, the user may be able to modify the spatial frequency and speed around this region to narrow down the threshold stimulus. The threshold stimulus may then be presented as a pair of spatial frequency and speed values. In further embodiments, a timer 265 is presented in the UI to allow the user to measure OKN recovery time after an intervening stimulus has been applied. In some embodiments the time is coupled to the photostress stimulus such that when a user applies the photostress, the timer automatically begins recording the time until OKN recovery.

Figure 10:
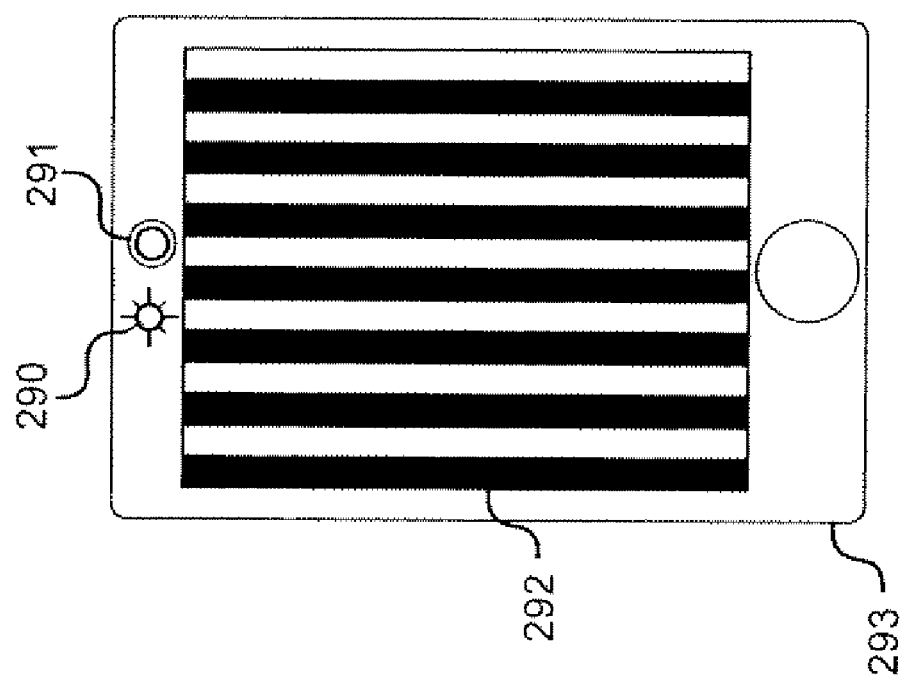
FIG. 10 illustrates a testing setup implemented in accordance with an embodiment of the invention.

FIG. 10 illustrates a test system for OKN testing implemented in accordance with an embodiment of the invention. In the illustrated embodiment, a smartphone, PDA, laptop, desktop, tablet, or other computer 293 is configured to display a test pattern 292 to a patient. In some embodiments, the computer 293 is connected to a administration system to allow a user, such as a practitioner, to control the display 292, as described above. In other embodiments, the computer 293 may be configured to display a predetermined visual stimulus 292, and modify the parameters of the stimulus 292 in an automatic fashion. For example, the computer 293 may be configured to display a predetermined battery of stimuli while a practitioner observes the patient. In still further embodiments, the computer 293 may be configured to determine a threshold OKN stimulus itself. For example, the computer may be equipped with an eye tracker, such as a camera 291, that allows it to determine when an OKN response is occurring in a viewer. By modulating various parameters, as described above, the computer can determine the threshold requirements for OKN response in the patient. A light source 290 may be used to provide a photostress to the patient to allow the system or a practitioner to measure OKN recovery after photostress, as described above.

Figure 11:
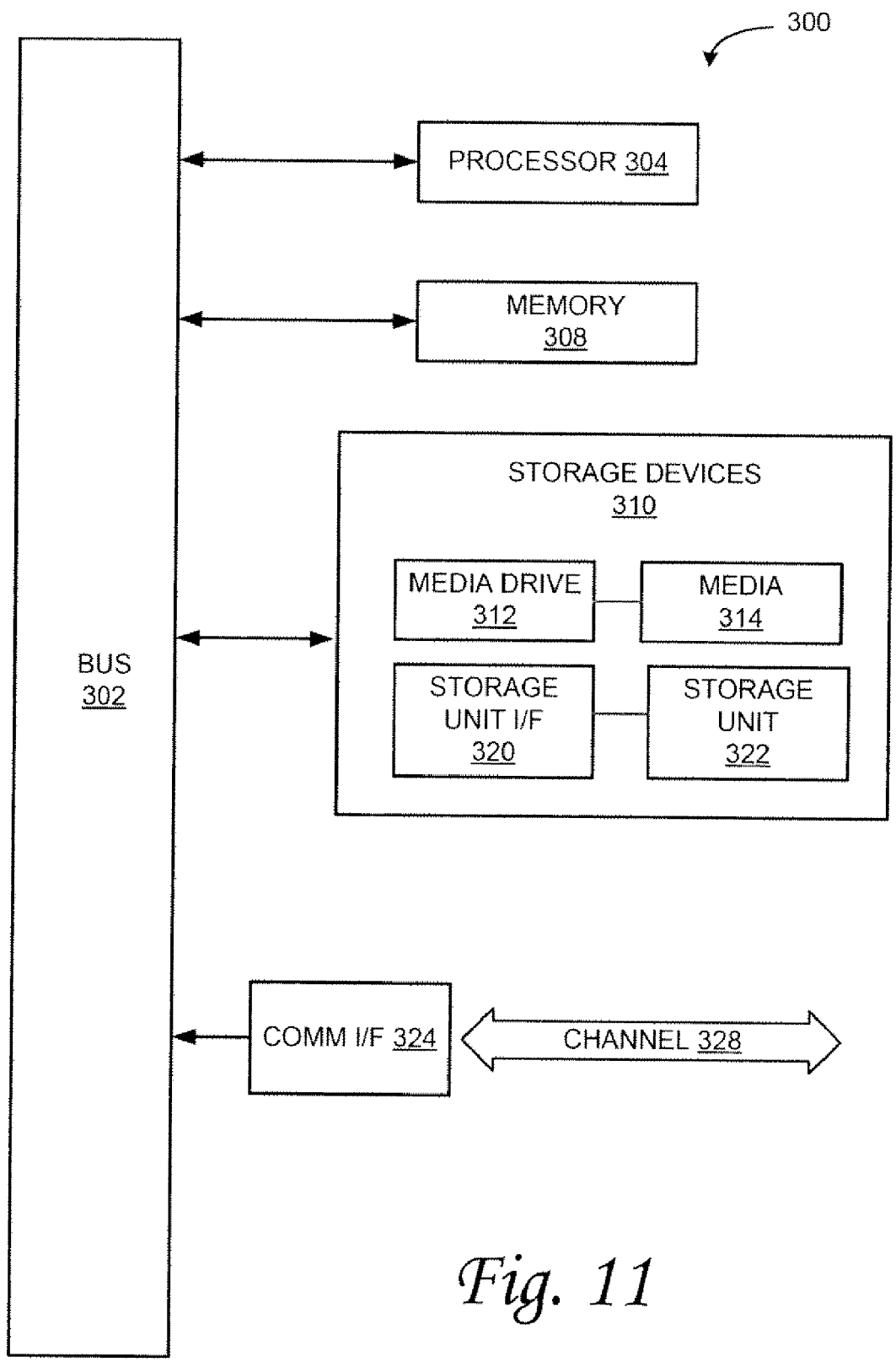
FIG. 11 illustrates an example computing module that may be used in implementing various features of embodiments of the invention.

As used herein, the term module might describe a given unit of functionality that can be performed in accordance with one or more embodiments of the present invention. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the invention are implemented in whole or in part using software, in one embodiment, these software elements can be implemented to operate with a computing or processing module capable of carrying out the functionality described with respect thereto. One such example computing module is shown in FIG. 11. Various embodiments are described in terms of this example-computing module 300. After reading this description, it will become apparent to a person skilled in the relevant art how to implement the invention using other computing modules or architectures.

Referring now to FIG. 11, computing module 300 may represent, for example, computing or processing capabilities found within desktop, laptop and notebook computers; handheld computing devices (RDA's, smart phones, cell phones, palmtops, etc.); mainframes, supercomputers, workstations or servers; or any other type of special-purpose or general-purpose computing devices as may be desirable or appropriate for a given application or environment. Computing module 300 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 300 might include, for example, one or more processors, controllers, control modules, or other processing devices, such as a processor 304. Processor 304 might be implemented using a general-purpose or special-purpose processing engine such as, for example, a microprocessor, controller, or other control logic. In the illustrated example, processor 304 is connected to a bus 302, although any communication medium can be used to facilitate interaction with other components of computing module 300 or to communicate externally.

Computing module 300 might also include one or more memory modules, simply referred to herein as main memory 308. For example, preferably random access memory (RAM) or other dynamic memory, might be used for storing information and instructions to be executed by processor 304. Main memory 308 might also be used for storing temporary variables or other intermediate information during execution of instructions to be executed by processor 304. Computing module 300 might likewise include a read only memory ("ROM") or other static storage device coupled to bus 302 for storing static information and instructions for processor 304.

The computing module 300 might also include one or more various forms of information storage mechanism 310, which might include, for example, a media drive 312 and a storage unit interface 320. The media drive 312 might include a drive or other mechanism to support fixed or removable storage media 314. For example, a hard disk drive, a floppy disk drive, a magnetic tape drive, an optical disk drive, a CD or DVD drive (R or RW), or other removable or fixed media drive might be provided. Accordingly, storage media 314 might include, for example, a hard disk, a floppy disk, magnetic tape, cartridge, optical disk, a CD or DVD, or other fixed or removable medium that is read by, written to or accessed by media drive 312. As these examples illustrate, the storage media 314 can include a computer usable storage medium having stored therein computer software or data.

In alternative embodiments, information storage mechanism 310 might include other similar instrumentalities for allowing computer programs or other instructions or data to be loaded into computing module 300. Such instrumentalities might include, for example, a fixed or removable storage unit 322 and an interface 320. Examples of such storage units 322 and interfaces 320 can include a program cartridge and cartridge interface removable memory (for example, a flash memory or other removable memory module) and memory slot, a PCMCIA slot and card, and other fixed or removable storage units 322 and interfaces 320 that allow software and data to be transferred from the storage unit 322 to computing module 300.

Computing module 300 might also include a communications interface 324. Communications interface 324 might be used to allow software and data to be transferred between computing module 300 and external devices. Examples of communications interface 324 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 324 might typically be carried on signals, which can be electronic, electromagnetic (which includes optical) or other signals capable of being exchanged by a given communications interface 324. These signals might be provided to communications interface 324 via a channel 328. This channel 328 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 308, storage unit 320, media 314, and channel 328. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 300 to perform features or functions of the present invention as discussed herein.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower ease is intended or required in instances where such broadening phrases may be absent. The use of the term "module" does not in ply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. A method of measuring retinal or visual pathway function, comprising:
   stimulating optokinetic nystagmus by presenting a visual stimulus to a patient;
   modifying a first parameter of the visual stimulus:
   modifying a second parameter of the visual stimulus; and
   using the modified visual stimulus to determine a threshold stimulus for optokinetic nystagmus; wherein
   the first and second parameters are selected from a group of parameters comprising a pattern for the visual stimulus, a width of the visual stimulus, a distance between the visual stimulus and the patient, a spatial frequency of the visual stimulus, a rate of change or temporal frequency of the visual stimulus, a color or wavelength of the visual stimulus and a contrast between elements of the visual stimulus.

2. The method of claim 1, wherein the first parameter is changed as a function of the second parameter.

3. The method of claim 2, wherein the first parameter comprises the rate of change or temporal frequency of the visual stimulus and the second parameter comprises the spatial frequency of the visual stimulus.

4. The method of claim 3, wherein the rate of change or temporal frequency of the visual stimulus is reduced as the spatial frequency of the visual stimulus is increased.

5. The method of claim 1, further comprising
   presenting an intervening stimulus to the patient after determining the threshold stimulus for optokinetic nystagmus; and
   re-stimulating optokinetic nystagmus after the step of presenting the intervening stimulus.

6. The method of claim 1, further comprising:
   interrupting the optokinetic nystagmus response of the patient by presenting an intervening stimulus to the patient; and
   measuring a time to recover optokinetic nystagmus.

7. The method of claim wherein the intervening stimulus comprises a light source.

8. The method of claim 7, wherein the light source comprises the visual stimulus or a photostress light source separate from the visual stimulus.

9. The method of claim 8, wherein the light source is presented to the patient at a strobe frequency that interrupts the optokinetic nystagmus.

10. The method of claim 7, wherein the intervening stimulus is presented to the patient for between about 1 ms to 1 min.

11. The method of claim 7, wherein the intervening stimulus has an intensity between about 1 and 2000 tux.

12. The method of claim 7, wherein the visual stimulus is displayed on a display, and wherein the intervening stimulus is presented using a light source that is coplanar with the display.

13. The method of claim 7, wherein the visual stimulus is displayed on a display, and wherein the intervening stimulus is presented using a light source that is not coplanar with the display.

14. The method of claim 6, wherein the intervening stimulus comprises a chemical or pharmaceutical.

15. The method of claim 6, further comprising measuring a recovery threshold stimulus for optokinetic nystagmus after the time to recover optokinetic nystagmus.

16. The method of claim 6, further comprising detecting the optokinetic nystagmus using an eye tracker.

17. The method of claim 16, wherein the step of measuring the time to recover optokinetic nystagmus is performed using a timing device coupled to the eye tracker.

18. The method of claim 1, wherein the visual stimulus comprises a test target comprising a plurality of contrasting bars, a rectilinear grid of contrasting elements, or a curvilinear pattern of contrasting elements.

19. The method of claim 1, wherein the rate of change or temporal frequency of the visual stimulus determines an apparent translational speed of the contrasting bars, an apparent translational speed of the rectilinear grid of contrasting elements, or an apparent rotational speed of the curvilinear pattern of contrasting elements.

20. A non-transitory computer readable medium having computer executable program code embodied thereon, the computer executable program code configured to cause an optokinetic nystagmus test apparatus to perform the steps of:
   receiving test target parameters from a user;
   generating a visual stimulus to stimulate optokinetic nystagmus using the test target parameters;
   displaying the visual stimulus;
   modifying a first parameter of the visual stimulus;
   modifying a second parameter of the visual stimulus; and
   displaying the visual stimulus with the modified first and second parameters;
   wherein the first and second parameters are selected from a group of parameters comprising a pattern for the visual stimulus, a width of the visual stimulus, a distance between the visual stimulus and a patient, a spatial frequency of the visual stimulus, a rate of change or temporal frequency of the visual stimulus, a color or wavelength of the visual stimulus and a contrast between elements of the visual stimulus.

21. The computer readable medium of claim 20, wherein the first parameter is changed as a function of the second parameter.

22. The computer readable medium of claim 21, wherein the first parameter comprises the rate of change or temporal frequency of the visual stimulus and the second parameter comprises the spatial frequency of the visual stimulus.

23. The computer readable medium of claim 22, wherein the rate of change or temporal frequency of the visual stimulus is reduced as the spatial frequency of the visual stimulus is increased.

24. The computer readable medium of claim 21, wherein the first parameter comprises the rate of change or temporal frequency of the visual stimulus and the second parameter comprises the width of the visual stimulus test face.

25. The computer readable medium of claim 21, wherein the first parameter comprises the rate of change or temporal frequency of the visual stimulus and the second parameter comprises the distance between the visual stimulus and the patient.

26. The computer readable medium of claim 20, wherein the computer executable program code is further configured to cause the optokinetic nystagmus test apparatus to perform the steps of:
displaying an image of an eye of the patient;
displaying a threshold value for optokinetic nystagmus, the threshold value of optokinetic nystagmus comprising a threshold value for the spatial frequency of the visual stimulus and a threshold value for the rate of change or temporal frequency of the visual stimulus.

27. The computer readable medium of claim 26, wherein the threshold value of optokinetic nystagmus further comprises a threshold value for a width of the visual stimulus, a distance between the visual stimulus and the patient, a color or wavelength of the visual stimulus or a contrast between elements of the visual stimulus.

28. The computer readable medium of claim 20, wherein the computer executable program code is further configured to cause the optokinetic nystagmus test apparatus to perform the steps of:
interrupting the optokinetic nystagmus response of the patient by presenting an intervening stimulus to the patient; and
measuring a time to recover optokinetic nystagmus.

29. The computer readable medium of claim 28, wherein the computer executable program code is further configured to cause the optokinetic nystagmus test apparatus to perform the step of detecting the optokinetic nystagmus using an eye tracker.

30. The computer readable medium of claim 29, wherein the computer executable program code is further configured to cause the optokinetic nystagmus test apparatus to use a timing device coupled to the eye tracker to perform the step of measuring the time to recover optokinetic nystagmus.

31. An optokinetic nystagmus test system, comprising:
a display configured to display a visual stimulus to a patient;
a computer coupled to the display and comprising a non-transitory computer readable medium having computer executable program code embodied thereon, the computer executable program code configured to cause the system to perform the steps of:
receiving test target parameters from a user;
generating a visual stimulus to stimulate optokinetic nystagmus using the test target parameters;
displaying the visual stimulus;
modifying a first parameter of the visual stimulus;
modifying a second parameter of the visual stimulus; and
displaying the visual stimulus with the modified first and second parameters;
wherein the first and second parameters are selected from a group of parameters comprising a pattern for the visual stimulus, a width of the visual stimulus, a distance between the visual stimulus and a patient, a spatial frequency of the visual stimulus, a rate of change or temporal frequency of the visual stimulus, a color or wavelength of the visual stimulus and a contrast between elements of the visual stimulus.

32. The system of claim 31, wherein the first parameter is changed as a function of the second parameter.

33. The system of claim 31, wherein the first parameter comprises the rate of change or temporal frequency of the visual stimulus and the second parameter comprises the spatial frequency of the visual stimulus.

34. The system of claim 33, wherein the rate of change or temporal frequency of the visual stimulus is reduced as the spatial frequency of the visual stimulus is increased.

35. The system of claim 31, wherein the first parameter comprises the rate of change or temporal frequency of the visual stimulus and the second parameter comprises the width, height or area of the visual stimulus test face.

36. The system of claim 31, wherein the first parameter comprises the rate of change or temporal frequency of the visual stimulus and the second parameter comprises the distance between the visual stimulus and the patient.

37. The system of claim 31, wherein the computer executable program code is further configured to cause the system to perform the steps of
displaying an image of an eye of the patient;
displaying a threshold value for optokinetic nystagmus, the threshold value of optokinetic nystagmus comprising a threshold value for the spatial frequency of the visual stimulus and a threshold value for the rate of change or temporal frequency of the visual stimulus.

38. The system of claim 37, wherein the threshold value of optokinetic nystagmus further comprises a threshold value for a width, height or area of the visual stimulus test face, a distance between the visual stimulus and the patient, a color or wavelength of the visual stimulus or a contrast between elements of the visual stimulus.

39. The system of claim 31, wherein the computer executable program code is further configured to cause the system to perform the steps of:
interrupting the optokinetic nystagmus response of the patient by presenting an intervening stimulus to the patient; and
measuring a time to recover optokinetic nystagmus.

40. The system of claim 39, wherein the computer executable program code is further configured to cause the system to perform the step of detecting the optokinetic nystagmus using an eye tracker.

41. The system of claim 40, wherein the computer executable program code is further configured to cause the system to use a timing device coupled to the eye tracker to perform the step of measuring the time to recover optokinetic nystagmus.

* * * * *

UNITED STATES PATENT AND TRADEMARK OFFICE
CERTIFICATE OF CORRECTION

| | | |
|---|---|---|
| PATENT NO. | : 7,918,558 B1 | |
| APPLICATION NO. | : 12/841849 | |
| DATED | : April 5, 2011 | |
| INVENTOR(S) | : Legerton | |

It is certified that error appears in the above-identified patent and that said Letters Patent is hereby corrected as shown below:

In Claim No. 11, please delete "tux" and replace with "lux"

Signed and Sealed this
Thirty-first Day of May, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,918,558 B1 | |
| APPLICATION NO. | : 12/841849 | |
| DATED | : April 5, 2011 | |
| INVENTOR(S) | : Legerton | |

It is certified that error appears in the above-identified patent and that said Letters Patent is hereby corrected as shown below:

Column 10, line 23 (claim 11, line 2) please delete "tux" and replace with "lux"

This certificate supersedes the Certificate of Correction issued May 31, 2011.

Signed and Sealed this
Twenty-eighth Day of June, 2011

David J. Kappos
*Director of the United States Patent and Trademark Office*